(12) United States Patent
Barbour et al.

(10) Patent No.: US 7,094,391 B1
(45) Date of Patent: Aug. 22, 2006

(54) **COMPOSITIONS AND METHODS FOR ADMINISTERING *BORRELIA BURGDORFERI* ANTIGENS**

(75) Inventors: Alan G. Barbour, San Antonio, TX (US); Catherine J. Luke, San Antonio, TX (US)

(73) Assignee: The University of Texas System, Austin, TX (US)

( * ) Notice: Subject to any disclaimer, the term of this patent is extended or adjusted under 35 U.S.C. 154(b) by 0 days.

(21) Appl. No.: 08/588,637

(22) Filed: Jan. 19, 1996

Related U.S. Application Data

(63) Continuation-in-part of application No. 08/079,601, filed on Jun. 22, 1993, now Pat. No. 5,523,089, which is a continuation of application No. 07/924,798, filed on Aug. 6, 1992, now abandoned, which is a continuation of application No. 07/422,881, filed on Oct. 18, 1989, now abandoned.

(30) Foreign Application Priority Data

Oct. 24, 1988 (DK) .................................. 5902/88

(51) Int. Cl.
*A61K 49/00* (2006.01)
*A61K 39/00* (2006.01)
*A61K 39/02* (2006.01)
*A61K 39/002* (2006.01)

(52) U.S. Cl. .................... 424/9.1; 424/9.2; 424/184.1; 424/190.1; 424/191.1; 424/234.1; 424/263.1; 424/278.1; 435/69.3; 530/300; 530/350

(58) Field of Classification Search ............ 424/263.1, 424/184.1, 234.1, 9.1, 9.2, 190.1, 191.1, 424/278.1; 435/69.3; 530/300, 350
See application file for complete search history.

(56) References Cited

U.S. PATENT DOCUMENTS 4,320,115 A * 3/1982 Bijlenga .................. 424/224.1
5,178,859 A * 1/1993 Simon et al. ............... 424/85.8
5,523,089 A * 6/1996 Bergstrom et al. ........ 424/262.1

FOREIGN PATENT DOCUMENTS

WO 90/02282 * 3/1990
WO 92/00055 * 1/1992

OTHER PUBLICATIONS

Wilske et al Annals of the New York Academy of Sciences 539: 126-143, 1988.*
Benach et al The Journal of Immunology 140: 265-272, 1988.*
Burgess, EC. Annals of New York Academy of Sciences, vol. 539. 1988 pp. 235-243.*
SN Cohen. Immunization. Chapter 43 in: Basic & Clinical Immunology, 3rd ed. Fudenberg HH, Stites DP, Caldwell JL, Wells JV (editors). Lange Medical Publications, 1980.*
Yoshimura, H., et al. "Oral vaccine therapy for pneumococcal otitis media in an animal model." Archives of Otolaryngology Head and Neck Surgery, vol. 117, No. 8, pp. 889-894, 1991.*
Muir, W., et al. "Induction of specific IgA responses in rats after oral vaccination with biodegradable microspheres containing a recombinant protein." Immunology Letters, vol. 42, No. 3, pp. 203-207, 1994.*
Valentine, P.J., et al. "Induction of SIV capsid-specific CTL and mucosal sIgA in mice immunized with a recombinant *S. typhimurium aroA* mutant." Vaccine, vol. 14, No. 2, pp. 138-146, 1996.*
Fujihashi, K., et al. "Gamma/delta T cell-deficient mice have impaired mucosal immunoglobulin A responses." Journal of Experimental Medicine, vol. 183, No. 4, pp. 1929-1935, 1996.*
Tuboly, T., et al. "Potential viral vectors for the stimulation of mucosal antibody responses against enteric viral antigens in pigs." Research in Veterinary Science, vol. 54, No. 3, pp. 345-350, 1993.*
Crawford, M. "Wistar proposes U.S. test of rabies vaccine." Science, vol. 240, No. 4854, p. 877(1), May 13, 1998.*
Dev. Biol. Stand., vol. 41, pp. 141-148, 1978.*

* cited by examiner

*Primary Examiner*—Rodney P Swartz
(74) *Attorney, Agent, or Firm*—Frommer Lawrence & Haug; Thomas J. Kowalski

(57) ABSTRACT

Mucosal administration of OspA and compositions therefor are disclosed and claimed. More particularly, oral administration of OspA and compositions therefor for eliciting an immunological response against *Borrelia burgdorferi*, such as a protective response preventive of Lyme disease are disclosed and claimed. Thus, oral Lyme disease vaccines or immunological compositions and methods of use are disclosed and claimed.

7 Claims, 1 Drawing Sheet

COMPOSITIONS AND METHODS FOR ADMINISTERING *BORRELIA BURGDORFERI* ANTIGENS

RELATED APPLICATIONS

Figure 1A:
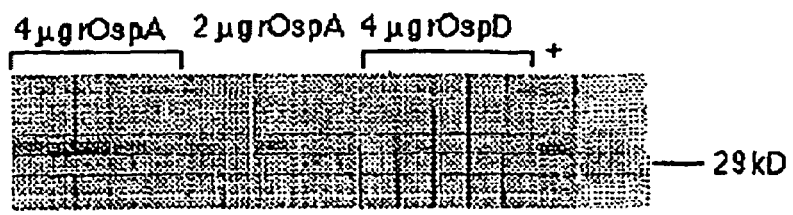

This application is a continuation-in-part of application Ser. No. 08/079,601, filed Jun. 22, 1993, now U.S. Pat. No. 5,523,089, which is a continuation of U.S. application Ser. No. 07/924,798, filed Aug. 6, 1992, now abandoned, which is a continuation of U.S. application Ser. No. 07/422,881, filed Oct. 18, 1989, now abandoned, claiming priority from Danish application 5902/88, filed Oct. 24, 1988.

Reference is made to U.S. application Ser. No. 08/320, 416, filed Oct. 3, 1994, now U.S. Pat. No. 5,582,990, U.S. application Ser. No. 08/137,175, filed Oct. 26, 1993, now U.S. Pat. No. 5,777,095, pending U.S. application Ser. No. 08/262,220, filed Jun. 20, 1994, PCT/US95/07665, U.S. application Ser. No. 08/373,455, filed Jan. 17, 1995, now abandoned, PCT/US92/08697, and WO 90/04411; each of which is hereby incorporated herein by reference.

STATEMENT OF GOVERNMENT SUPPORT

This work was supported by NIH grant RO1 AI37248, and without any admission the U.S. Government may have certain rights.

FIELD OF THE INVENTION

This invention relates to methods for administering *Borrelia burgdorferi* antigens. More particularly, this invention relates to methods for administering *Borrelia burgdorferi* OspA (outer surface protein A), especially recombinant OspA (rOspA), and/or OspD (outer surface protein D), especially recombinant OspD (rOspD), or fragments thereof; and to compositions employed in such methods. Even more particularly, this invention relates to methods for mucosally administering OspA such as rOspA, e.g., for orally administering OspA, e.g., rOspA, especially to a host mammal susceptible to Lyme disease infection, e.g., humans, domesticated animals, and even non-domesticated or wild animals (since the present invention provides that OspA or rOspA can be left in the wild with bait so as to allow for administration without contact with the wild animals, thereby diminishing the *Borrelia burgdorferi* population and ergo the ability for *Borrelia burgdorferi* and Lyme disease to be transmitted to domesticated animals and humans); and, to compositions therefor.

BACKGROUND OF THE INVENTION

Lyme disease is a multisystem illness, transmitted by ticks of the *Ixodes ricinus* complex. The spirochaete *Borrelia burgdorferi* sensu lato is the aetiologic agent of Lyme disease, which is now the most common arthropodborne disease in the United States, and is endemic in Central Europe (1). Although curable by antibiotic therapy in its early stages, if Lyme disease is allowed to progress, cardiac, neurological and joint abnormalities can arise. Investigations into the development of a human vaccine for Lyme disease are under way. The outer surface lipoprotein OspA of *Borrelia burgdorferi* is the current major candidate molecule for development of such a vaccine. Recombinant OspA lipoprotein (rOspA) is known to elicit a protective immune response in mice against challenge by infectious *B. burgdorferi* (2,3). OspA is currently undergoing human field trials as a subcutaneously administered vaccine in the United States (4).

Above-cited application Ser. No. 08/373,455 and PCT/US92/08697 relate to rOspA vaccines, especially lipidated rOspA, and methods for expressing DNA encoding OspA or fragments thereof. Above-cited application Ser. No. 08/320, 416 and WO 90/04411 relate to DNA encoding OspA, the amino acid sequence of OspA, synthetic OspA, compositions containing OspA or synthetic OspA, and methods of using such compositions. And, the other above-cited applications relate to DNA encoding other *Borrelia* antigens or other Osps, or to DNA encoding useful fragments of OspA or of other Osps or of other *Borrelia* antigens, amino acid sequences thereof, compositions containing such fragments or other Osps, and methods for using such compositions; and, such DNA can be used in the methods of Ser. No. 08/373,455 or PCT/US92/08697 to produce OspA, other *Borrelia* antigens or Osps, or fragments thereof, for use in this invention.

Alternative vaccination strategies are desirable as such provide alternative routes to administration, thereby allowing administration to humans who may be sensitive to injections, e.g., young children or infants, or to other hosts with whom there is difficulty giving injections, e.g., wild animals, and even domestic animals.

OspA administered orally in an *Escherichia coli* was capable of stimulating a mucosal immune response that protected mice against challenge with infectious *B. burgdorferi* (5). More recently, Dunne et al. reported oral immunization of mice with an attenuated strain of *Salmonella typhimurium* expressing OspA, which appeared to protect 80% of the mice from challenge by infectious *B. burgdorferi* (6). Mucosal immunity was also demonstrated following intra-nasal administration of recombinant BCG expressing OspA (7). However, rOspA in *E. coli*, *Salmonella* expressing OspA, and, BCG expressing OspA, are not viable products for usefully administering rOspA to humans or animals—domestic or wild—as *E. coli*, *Salmonella* and BCG are not safe or approved for administration to humans or animals (and even if attenuated, there is nonetheless a chance of reversion); and, one cannot be certain if any immunological response in these prior publications was not an effect of an adjuvanting or immunological stimulating effect of *E. coli*, *Salmonella* or BCG (note, for instance, how LPS is known to have an adjuvanting effect).

Thus, heretofore the art has not taught or suggested mucosal, preferably oral, administration to a mammalian host—domesticated or wild animal or human—susceptible to Lyme disease, of *Borrelia* antigen or immunological fragment thereof, e.g., OspA, preferably rOspA, more preferably lipidated OspA or rOspA, preferably substantially free of other bacterial proteins and substantially free of lipopolysaccharide (LPS), in a suitable carrier or diluent in an amount sufficient to induce an immunological response preferably a protective immunological response, in the host, preferably without any necessity of using any immunogenicity-enhancing adjuvant; or compositions therefor; and, the protection by such administration herein demonstrated has not been heretofore taught or suggested. Further, heretofore the advantages of such oral administration, e.g., ease of administration to domestic animals and young children or infants by merely droppering into the mouth, ease of administration to wild animals by dropping bait containing the OspA or rOspA, has not been taught or suggested.

OBJECTS AND SUMMARY OF THE INVENTION

It is an object of the invention to provide methods and compositions for mucosally, e.g., orally administering to a mammalian host susceptible to Lyme Disease *Borrelia burgdorferi* isolated and/or purified *Borrelia* antigen or a fragment thereof, e.g., OspA, preferably rOspA, more preferably isolated and/or purified lipidated OspA or rOspA substantially free of other bacterial proteins, substantially free of LPS, in a carrier or diluent, in an amount sufficient to induce an immune response, preferably a protective immune response, and preferably without any necessity of adding or using any immunogenicity-enhancing adjuvant.

More particularly, it has been surprisingly found that OspA in a carrier or diluent orally administered induces a protective response against *Borrelia burgdorferi.*

Thus, in a broad sense, the invention provides a method for eliciting an immunological response comprising mucosally, preferably orally, administering an isolated and/or purified *Borrelia* antigen, or immunologically active fragment thereof in admixture with a suitable carrier or diluent, to a host susceptible to Lyme disease or *Borrelia* infection, and to compositions containing the antigen and carrier or diluent. Preferably the antigen or fragment is lipidated such that the composition and method need not contain or use an adjuvant. The compositions can be in solid or liquid form.

The present invention therefore preferably provides a method for inducing an immunological response, preferably a protective immunological response, in a host susceptible to Lyme disease comprising mucosally administering a composition comprising an immunologically effective, preferably for protection, amount of *Borrelia burgdorferi* OspA and a suitable carrier or diluent. The OspA can be rOspA, and is preferably lipidated, substantially free of other bacterial proteins, and substantially free of LPS. The composition need not, and preferably does not, contain any adjuvant. The mucosally administering is preferably by orally administering. The concepts of substantially free of LPS and substantially free of other bacterial proteins is as in the aforementioned and cited "Related Applications". The carrier or diluent can be a liquid vehicle such as PBS, or bait suitable for wild animals. The *Borrelia* antigen or fragment, e.g., OspA, can be present in amounts determined by factors well-known in the medical or veterinary arts, or as disclosed in the aforementioned and cited related applications, e.g., 0.5–500 μg; presently preferably 0.5 to 50 μg, for instance, 1–10 μg.

Accordingly, the present invention more preferably provides a method for inducing an immunological response, preferably a protective immunological response, in a host susceptible to Lyme disease comprising orally administering a composition consisting essentially of a carrier or diluent and recombinant lipidated *Borrelia burgdorferi* OspA which is isolated and/or purified, substantially free of other bacterial proteins and substantially free of LPS.

Compositions employed in the methods are comprehended by the invention.

Fragments of OspA which induce a protective response can also be used in the practice of the invention. As to *Borrelia* antigens and fragments thereof, the reader is directed to the applications cited under "Related Applications" and incorporated herein by reference.

Other objects and embodiments are disclosed or are obvious from the following Detailed Description.

BRIEF DESCRIPTION OF DRAWINGS

In the following Detailed Description reference is made to the accompanying Figures, incorporated herein by reference, wherein:

FIG. 1(A) shows Immunoblots of sera from mice immunized o.g. with rOspA or rOspD showing antibody to rOspA in the mice with rOspA (24 μg rOspA was loaded onto a preparative PAGE gel which was subsequently immunoblotted. Sera were diluted 1:100 in PBS containing 0.3% milk. Positive control (+) was monclonal antibody (MAb) H5332, specific for OspA, hybridoma supernatant diluted 1:50 in PBS/milk. Negative control (−) was MAb H1C8, specific for OspD, hybridoma supernatant, diluted 1:50 in PBS/milk);

FIG. 1(B) shows Immunblots of sera from mice immunized orogastrically (24 μg rOspD was loaded onto a preparative PAGE gel for immunoblotting. Sera were diluted 1:100 in PBS/milk. Positive control (+) was MAb H1C8); and FIG. 1(C) shows Immunoblots of sera from mice immunized subcutaneously with 4 μg rOspD (24 μg rOspD was loaded onto a preparative PAGE gel for immunoblotting. Sera were diluted 1:200 in PBS/milk. Positive control (+) was MAb H1C8); and FIG. 1(D) shows Immunoblots of sera from mice immunized orally or subcutaneously with rOspA and rOspD showing detection of IgA subclass immunoglobulin with an IgA-specific conjugate (Mouse sera were diluted 1:400 PBS/milk. IgG positive control (α-OspA +) control was MAb H5332 (IgG2a) hybridoma supernatant diluted 1:10 in PBS/milk, and the strip was incubated with an IgG-specific conjugate. IgG negative control (IgG −ve) was H5332 hybridoma supernatant, and the strip was incubated with the IgA-specific conjugate. Control for IgA-specific conjugate background (IgA −ve) was a strip incubated in PBS/milk and then in IgA-specific conjugate. IgA positive control was mouse myeloma protein TEPC15(IgAk)).

DETAILED DESCRIPTION

As discussed above, the invention preferably provides methods for immunizing or vaccinating a host susceptible to Lyme disease, e.g., a mammalian host, against *Borrelia burgdorferi* and accordingly Lyme Disease, by mucosally, preferably orally, administering OspA, preferably lipidated OspA, more preferably lipidated OspA substantially free of other bacterial proteins and substantially free of LPS, most preferably lipidated rOspA substantially free of other bacterial proteins and substantially free of LPS, in a suitable carrier or diluent, and preferably without any necessity of there being any immunogenicity-enhancing adjuvant present.

Indeed, as shown in Example 1 recombinant outer surface protein A (rOspA) from *Borrelia burgdorferi* strain B31, substantially free of other bacterial proteins and substantially free of LPS, was administered orally to mice at doses of 4.0 μg and 2.0 μg respectively, in carrier or diluent (PBS) without any adjuvant. Mice were challenged with $10^4$ infectious *Borrelia burgdorferi* and organs were cultured to determine protection. In 2 experiments, 8/8 mice that received 4.0 μg of rOspA were protected against infection by *B. burgdorferi,* 6/7 mice that received 2.0 μg rOspA were protected 0/8 of the mice that received 4.0 μg rOspD were protected. Enzyme linked immunosorbent assay (ELISA) and immunoblot analysis revealed that those mice which received rOspA orally mounted a specific antibody response against rOspA and that the sera contained antibodies of the IgA immunoglobulin subclass. In contrast, no antibody response to rOspD was detectable in the sera from those mice immunized orogastrically with OspD. Sera from mice immunized with rOspD subcutaneously, however, did contain rOspD-specific antibody detectable on immunoblots. Sera from the mice given rOspA orally also inhibited growth of *B. burgdorferi* B31 in vitro.

As shown by present dog and human trials from the previous work with mice (3), it is clear that mice are now a suitable animal model with respect to *Borrelia burgdorferi* and Lyme disease for extrapolation to domestic animals, humans, and other animals susceptible to Lyme disease or *Borrelia burgdorferi* infection (e.g., wild animals such as deer).

In view of the broad nature of the invention, i.e., that the invention is applicable to *Borrelia* antigens and immunologically active fragments thereof, discussion herein directed to OspA is intended to encompass the broad nature of the invention, i.e., "OspA" is exemplary and can be read in this specification to include "*Borrelia* antigen or an immunological fragment thereof".

The mucosal administration in the present invention is preferably oral administration; but, the invention broadly comprehends oral, nasal, peroral, sublingual, perlingual, intragastric, anal, vaginal, alveolar, gingival, olfactory, respiratory or other mucosal routes of administration.

In the present invention OspA (or broadly the *Borrelia* antigen or immunologically active fragment thereof) can be administered in dosages and by techniques well known to those skilled in the medical or veterinary arts taking into consideration such factors as the age, sex, weight, species and condition of the particular patient, and the route of administration. OspA (or antigen or fragment thereof) can be administered alone, or can be co-administered or sequentially administered with other antigens; and, the OspA (or antigen or fragment thereof) can be sequentially administered, e.g., each Spring as the "Lyme disease season" is about to begin.

In the present invention the OspA (or antigen or fragment thereof) can be in solutions, suspensions, emulsions, syrups, elixirs, capsules (including gelcaps-gelatin capsule containing a liquid OspA, antigen or fragment preparation), tablets, hard-candy-like preparations, and the like. The OspA (or antigen or fragment) may be in admixture with a suitable carrier, diluent, or excipient such as sterile water, physiological saline, PBS, glucose or the like. The compositions can also be lyophilized. The compositions can contain auxiliary substances such as wetting or emulsifying agents, pH buffering agents, adjuvants, gelling or viscosity enhancing additives, preservatives, flavoring agents, colors, and the like, depending upon the route of administration, antigen and the preparation desired (e.g., adjuvant is not presently preferred especially for lipidated antigens or fragments thereof; but, may be useful for non-lipidated antigens or fragments thereof).

Standard texts, such as "REMINGTON'S PHARMACEUTICAL SCIENCE", 17th edition, 1985, incorporated herein by reference, may be consulted to prepare suitable preparations, without undue experimentation. Suitable dosages can also be based upon the examples below, and upon the documents herein cited. In view of such standard texts as "REMINGTONS'S", and such commercially available products as Dristan® nasal spray, Vancenase® AQ nasal spray and the like, no undue experimentation is required to nasally administer OspA (or *Borrelia* antigen or fragment thereof); or to make preparations therefor. And, in view of such standard texts as "REMINGTON'S" and commercially available anal suppository and vaginal suppository products, no undue experimentation is required to anally or vaginally administer OspA (or *Borrelia* antigen or fragment thereof); or to make preparations therefor.

Further, as shown herein, mucosal administration of OspA (or *Borrelia* antigen or fragment thereof) in accordance with the invention stimulates an immune or antibody response in humans or animals. This antibody response means that the inventive method can be used for merely stimulating an immune response (as opposed to also being a protective response) because the resultant antibodies (without protection) are nonetheless useful. From eliciting antibodies, by techniques well-known in the art, monoclonal antibodies can be prepared; and, those monoclonal antibodies, can be employed in well known antibody binding assays, diagnostic kits or tests to determine the presence or absence of *Borrelia burgdorferi* or to determine whether an immune response to the spirochete has simply been stimulated. Those monoclonal antibodies can also be employed in immunoadsorption chromatography to recover or isolate *Borrelia* antigens such as OspA.

Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H. U.S. Pat. No. 4,376,110, issued Mar. 8, 1983; incorporated herein by reference. Monoclonal antibodies have also been used to recover materials by immunoadsorption chromatography, e.g., Milstein, C. 1980, Scientific American 243:66, 70, incorporated herein by reference.

Accordingly, the inventive methods and products therefrom have several hereinstated utilities. Other utilities also exist for embodiments of the invention.

A better understanding of the present invention and of its many advantages will be had from the following examples, given by way of illustration.

EXAMPLES

Example 1

Oral Administration of OspA and OspD

Materials & Methods

*Borrelia burgdorferi*: *B. burgdorferi* strain Sh-2-82, a strain from the same OspA serogroup as B31, was used for infectious challenge (8). Sh-2-82 had been cloned by limiting dilution and passaged in SCID mice and was stored frozen at −135° C. in BSK II containing 10% of v/v DMSO (ATCC, Rockville, Md.) until needed. Stain B311 is a clonal, high-passage, non-infectious derivative of B31 (ATCC 35210) that produces OspA and OspB (9). HB19R1 is a high passage, non-infectious derivative of HB19 selected for by growth in the presence of antibodies to OspA and OspA (15). HB19R1 does not produce OspA or OspB but produces OspD.

Recombinant lipoproteins: Recombinant, lipidated outer surface proteins rOspA and rOspD from *Borrelia burgdorferi* B31 were obtained and purified as described previously (3) and were provided by Dr. R. Huebner of Connaught Laboratories, Swiftwater, Pa. rOspA was provided in 50 mM Tris, pH 7.5; 10 mM NaCl; 2 mM EDTA; 0.3% Triton X-100. rOspD buffer was at pH 6.5, but was otherwise identical to the rOspA buffer.

Immunization: Female C3H/HeN mice were obtained from Harlan laboratories (Indianapolis, Ind.). At age 10 weeks, mice were vaccinated with rOspA or rOspD from *Borrelia burgdorferi* B31. Administration of vaccine was via the oral route, using 0.5 ml rOspA diluted in sterile PBS (pH 7.4). Vaccine was delivered through 20 gauge, 1.5 in stainless gavage needles (Popper & Son Inc., NY).

Challenge with infectious *B. burgdorferi*: Mice were injected intra-dermally at the base of the tail with $10^4$ (100 times the $ID_{50}$) *B. burgdorferi* Sh-2-82 (3). 10 days after challenge with infectious *B. burgdorferi* Sh-2-82, mice were sacrificed. Mice were anaesthetized with Metofane (Pitman-Moore Inc., Mundelein, Ill.), exsanguinated by cardiac puncture and were euthanized by cervical dislocation. Heart, urinary bladder and cross-cuttings of the tibiotarsal joints were aseptically removed. These organs, and 0.5 ml plasma, were cultured in BSK II containing 10% rabbit serum, and 35° C. Cultures were examined for the presence of spirochetes by phase contrast microscopy on day 5 after sacrifice and were examined up to day 16. Cultures were considered negative if no spirochetes were seen in 20 high power fields.

Enzyme linked immunosorbent assay (ELISA): Mouse sera were subjected to a whole wet cell ELISA, described previously (9). Plates were coated at 4° C. for 48h with $10^7$ *B. burgdorferi* strain B311 cells (9) per well, in bicarbonate coating buffer (15 mM $Na_2CO_3$, 35 mM $NaHCO_3$, 3 mM $NaN_3$, pH 9.6) or with rOspA as described by Erdile et al. (3). Serial dilutions of mouse sera were made in PBS (pH 7.4) containing 1% w/v non-fat dried milk. Secondary antibody was either goat anti-mouse IgG+IgA+IgM (H+ L) or goat anti-mouse IgA (H+ L), conjugated to alkaline phosphatase (Zymed Laboratories, South San Francisco, Calif.) used at a dilution of 1:1000 in PBS/1% milk.

Polyacrylamide gel electrophoresis (PAGE) and immunoblotting: PAGE and immunoblotting were carried out as described (10,11). 24 µg of recombinant proteins rOspA and rOspD were run on preparative SDS-PAGE gels and were then transferred onto nitrocellulose membranes. Immunoblots were dried and stored at 4° C. until needed. IgA positive control was purified mouse myeloma protein TEPC15 (IgAk). Monoclonal antibody hybridoma supernatants from H5332 and H1C8 were used at a dilution of 1: 10 in 1% PBS/milk, and served as positive controls for rOspA and rOspD, respectively.

Growth Inhibition Assay: In vitro growth inhibitory activity of mouse sera was assessed as described by Sadziene et al (12). 2 hemolytic units (HU) of unheated guinea pig complement (Calbiochem-Novabiochem Corporation, San Diego, Calif.) was added to each well to give a final concentration of 10 HU/ml of medium after addition of antibody. Microtiter wells were monitored visually for changes in the color of the phenol red indicator and by phase-contrast microscopy of wet mounts. The growth inhibitory (GI) titer was defined as the lowest dilution of antiserum that resulted in pink instead of yellow wells and represented at least 20-fold fewer cells than in control (no immune serum) wells.

Trypsin digestion: Lipidated recombinant proteins rOspA and rOspD were both diluted to a concentration of 250 µg/ml in Osp dilution buffer. One hundred microliter volumes were dispensed into wells of a 96-well microtiter plate. L-1 Tosylamide-2-phenylethyl chloromethyl ketone (TPCK)—treated trypsin (Sigma Chemical Co., St. Louis, Mo.) stock solution was diluted in trypsin digestion buffer, pH 8.0, (13) (10 mM sodium phosphate pH 6.0, 50 mM NaCl, 20 mM Tris-HCL). To each well was added 100 µl 3×SDS-PAGE solubilization buffer (0.19M Tris, pH 6.8, 30% v/v glycerol, 3% w/v SDS, 0.0015% w/v bromophenol blue) containing 15 µl 1 M dithiothreitol (DTT), and the samples were immediately transferred to microfuge tubes and then frozen. Samples were then boiled for 3 minutes immediately prior to loading onto a 15% polyacrylamide gel for electrophoresis.

Results

Immunization:

Experiment 1: Mice were vaccinated with either 4 µg rOspA, 2 µg rOspA or 4 µg rOspA on day 1, and were given an identical dose of vaccine on days 2 and 4. 12 days after the initial vaccination, the mice were bled from the tail. Mice were boosted with identical vaccine on day 21 and were bled again from the tail on day 31.

Experiment 2: Mice were immunized as in Experiment 1, except the first tail bleed was done on 8 days after the initial immunization, there was an additional booster dose on day 22, and the second bleed was done on day 25.

Challenge with infectious *B. burgdorferi*: To determine whether oral immunization with the different recombinant osps resulted in protection of mice against infectious challenge, 32 days after the initial vaccination, mice were challenged intradermally with $10^4$ *B. burgdorferi* Sh2. Following sacrifice, cultures from mice were first examined by phase contrast microscopy after 5 days, and were examined again on days 7, 8, 10, 12 and 16, for the presence of spirochetes. By day 5, spirochetes were evident in the heart, bladder and joint cultures from all 5 of the mice that were given rOspD, and all other cultures were negative. The culture data on day 16 is presented in Table 1.

ELISAs: Sera from the immunized mice were subjected to ELISA to investigate the humoral response to oral immunization with rOspA or rOspD. Titers were compared to those from sera of mice immunized subcutaneously. Sera were diluted by two-fold serial dilution beginning at 1:20, through 1:40,960. Titers obtained from the second bleed in both Experiments 1 and 2 are shown in Table 1. Sera from Experiment 2 were also subjected to ELISA with non-lipidated rOspA, using a second antibody specific for murine IgA.

Figure 1B:
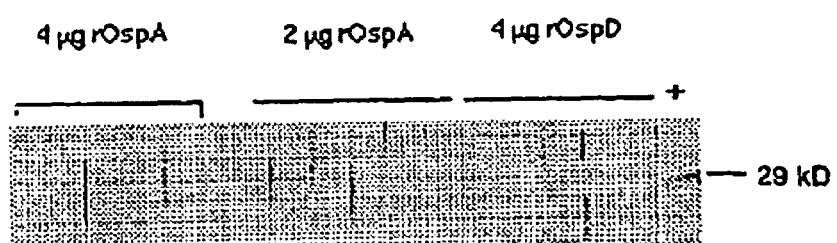
Figure 1C:
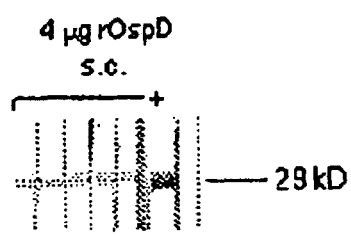
Figure 1D:
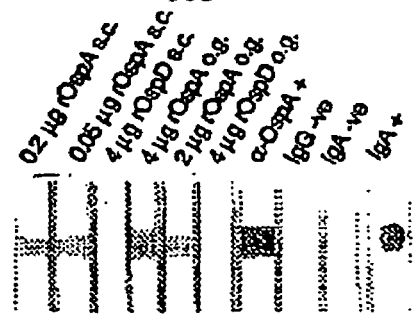

Immunoblots: Specificity of the antibody response of the mice to oral immunization with rOspA or rOspD was investigated by immunoblot. When sera from orally immunized mice was required, only sera from experiment 2 were used. Sera from the mice immunized via the oral route with 4 µg rOspA had a titer of 1:1600 by immunoblot. Sera from 2 of the mice immunized with 2 µg rOspA had an immunoblot titer of 1:1600, and the titer of the sera from the other 3 mice was 1:400. FIG. 1A shows binding of antibodies in the sera from orally immunized mice to rOspA. Sera from the mice that were immunized orally with rOspD did not have antibodies that bound to rOspD in immunoblots (FIG. 1B). However, sera from mice that had been immunized subcutaneously with 4.0 µg rOspD alone did contain antibodies that bound rOspD in immunoblots (FIG. 1C). Sera from the mice immunized by either the oral or subcutaneous route (diluted 1 in 400) were also subjected to immunoblot using a conjugate specific for murine IgA to compare the relative amounts of this immunoglobulin subclass in sera from animals immunized via different routes (FIG. 1D).

Growth Inhibition Assays: Sera from mice immunized orally with OspA or rOspD and those immunized subcutaneously with rOspD were assessed by GIA to determine whether the antibodies in the sera could inhibit growth of *B. burgdorferi* in vitro. Sera from the mice immunized orally with 4 µg rOspA inhibited growth of the OspA-producing strain *B. burgdorferi* B311 in vitro at a dilution of 1 in 128. The same sera, however, did not inhibit the growth of strain HB19-R1 in vitro. This strain does not produce OspA, but produces an increased amount of OspD compared to the parent HB19 strain. Sera from the mice that received 2 µg rOspA orally had a reciprocal GI titer 4 fold less than that of the mice that received 4 µg rOspA by this route, and did not have any effect on the growth of strain HB19-R1. Sera from the mice that received rOspD via the oral route did not inhibit the growth of either B311 or HB19-R1 in vitro, whereas sera from mice immunized subcutaneously with rOspD inhibited growth of HB19-R1 up to a dilution of 1 in 32. The GI titers obtained are summarized in Table 2.

Sensitives of rOspA and rOspD to trypsin: The immunoblot, ELISA and GI data suggested that rOspD administered subcutaneously resulted in the production of OspD-specific antibodies, but rOspD administered orally did not. It was decided to investigate the relative trypsin sensitivities of rOspA and rOspD in an attempt to explain why rOspA stimulated antibody production when given orally but rOspD did not. rOspA at a concentration of 250 µg ml$^{-1}$ in Osp buffer was digested into peptide fragments by 0.125 µg ml$^{-1}$ trypsin; this was determined by polyacrylamide gel electrophoresis. rOspD was digested into peptide fragments by 0.03125 µg ml$^{-1}$ trypsin under the same conditions.

Table 1. ELISA titers and protection data from study in which mice were immunized orally with rOspA or rOspD of *Borrelia burgdorferi* B31

| Immunogen | ELISA titer[a] | Positive Cultures | | | |
|---|---|---|---|---|---|
| | | plasma | heart | bladder | joint |
| Expt. 1: | | | | | |
| rOspD, 4 µg | 20 | 0/3 | 3/3 | 3/3 | 3/3 |
| rOspA, 4 µg | 640 | 0/3 | 0/3 | 0/3 | 0/3 |
| rOspA, 4 µg | 320 | 0/2 | 1/2* | 1/2* | 1/2* |
| Expt. 2: | | | | | |
| rOspD, 4 µg | 20 | 3/5 | 5/5 | 5/5 | 5/5 |
| rOspA, 4 µg | 1470 | 0/5 | 0/5 | 0/5 | 0/5 |
| rOspA, 2 µg | 485 | 0/5 | 0/5 | 0/5 | 0/5 |

[a]ELISA titers presented are the geometric mean titers from the second bleed (3 days post-boost).
*Positive cultures were obtained from the same mouse Table 2. Growth inhibitory titers of sera from mice immunized orally or subcutaneously with recombinant *Borrelia burgdorferi* lipoproteins

| Immunogen | Route | Growth inhibitory titers | |
|---|---|---|---|
| | | B311[a] | HB19R1[b] |
| 4.0 µg rOspD | oral | ≦8 | ≦8 |
| 4.0 µg rOspA | oral | 128 | ≦8 |
| 2.0 µg rOspA | oral | 32 | ≦8 |
| 4.0 µg rOspD | subcutaneous | ≦8 | 32 |

[a]B311 expresses OspA but not OspD
[b]HB19R1 expresses OspD but not OspA

Discussion

Investigations into the development of a vaccine for Lyme disease currently focus on OspA as a candidate vaccine. In human field trials, rOspA was administered subcutaneously (3). The present invention provides alternative routes of administration of a vaccine or immunological composition. Stimulation of the mucosal immune system by intra-nasal administration of a recombinant BCG vector expressing OspA has been demonstrated (7) and Dunne and co-workers recently reported oral immunization of mice with an attenuated strain of *Salmonella typhimurium* expressing OspA (6). However, in addition to safety and other issues whereby the work of Dunne and Langermann provide nothing of any practical utility and only mere laboratory curiosities, without any true proof of results being from OspA (and not from immunity enhancement from other materials present in their preparations administered), in the work of Dunne, Langermann and others, not all the experimental animals were protected against infectious challenge by the alleged vaccine in their studies, whereas the herein Applicants report 100% protection of mice against infection by *B. burgdorferi* by oral administration of rOspA alone (without adjuvant or additional ingredients which could enhance immunogenicity).

ELISA and immunoblot studies showed a strong antibody response to OspA in the immunized animals, of both IgG and IgA immunoglobulin subclasses following booster administrations of vaccine or immunological composition of the invention. The lipoprotein control group, that received rOspD via the same route, did not demonstrate a detectable antibody response to rOspD either by ELISA or immunoblot. In contrast, mice that were immunized subcutaneously with 4 µg rOspD produced an antibody response detectable by immunoblot at a serum dilution of 1:100. Of course, if lipidated or if adjuvanted, the OspD should elicit an immunological response, when administered by that route.

Sensitivities of rOspA and rOspD to trypsin and low pH were investigated in an attempt to explain the difference in immunogenicity of these lipoproteins when administered orally. It was thought that the gastric acidity or trypsin in the small intestine may affect these proteins differently and thereby influence the antibody response to them. It was found that, under the conditions examined here, that is, rOspA and rOspD resuspended in the Osp buffer, there was a four-fold difference in their sensitivities to trypsin. Although rOspA was slightly more resistant to trypsin digestion than rOspD, it did not appear that rOspD was dramatically more sensitive. rOspA appeared to be more sensitive to trypsin than had been reported by Dunn and co-workers, but in that case, the rOspA was not resuspended in Osp buffer. This buffer contains Triton X-100, which could increase the sensitivity of rOspaA to proteolytic cleavage.

The use of a single protein mucosal, preferably oral, vaccine or immunological composition has not been described or suggested for *B. burgdorferi* infection. Studies in which oral immunization against *B. burgdorferi* has been investigated have made use of bacterial carrier systems, namely, *Escherichia coli* and attenuated *Salmonella typhimurium* (5, 6). Because of safety, certainty of the result being from OspA, and ease and cost of preparation, it should be considered that the present invention is surprisingly more safe, certain, efficient and effective than the prior art. It is also possible that the host immune system would mount a response against antigens of the prior art carrier systems, and therefore reduce efficiency of vaccine antigen delivery upon repeated administrations of prior art compositions (or repeated performance of the prior art).

The molecular structure of rOspA lipoprotein may facilitate its absorption in the gastrointestinal tract, and stimulation of the mucosal immune system. It appears that gastric acidity does not affect the ability of OspA to be taken up and transported by cells in the gastrointestinal tract. There is evidence that proteins that are relatively resistant to gastric acid are good candidates for oral vaccines; for example, recombinant urease of *Helicobacter pylori* (14). It is not known whether rOspD is stable in acidic conditions. Such differences in biochemical properties of these proteins may explain the apparent failure of rOspD to elicit a detectable antibody response when administered via the oral route. The protection data from this study show that the rOspA administered mucosally, preferably orally, is 100% effective in eliciting a protective immune response in mice against challenge by infectious *B. burgdorferi*.

The simplicity and efficacy of oral administration in accordance with the present invention, as herein demonstrated, shows that oral immunization or vaccination of humans and animals—domestic or wild—is provided by the present invention.

Indeed, the present invention can diminish infection of wild animals. Infection of wild animals leads to infection of humans and domestic animals. *Borrelia burgdorferi* is well known for being transmitted by *Borrelia burgdorferi* infected deer bearing ticks. The ticks carry the bacteria to domestic animal or human hosts by the ticks being left by the deer in areas contacted by domestic animals or humans, and the ticks then biting and thus infecting the domestic animals or humans. Accordingly, suitable bait (e.g., food of wild animals susceptible to *Borrelia burgdorferi* infection such as food of deer) containing a *Borrelia* antigen or immunological fragment thereof, e.g., OspA could lead to vaccination of wild hosts, with the resultant diminishing of infection in such wild hosts, and the diminishing of spread of infection from such wild hosts to humans and domestic animals.

Additionally, since the herein protective results are from isolated, purified recombinant lipidated OspA without any adjuvant, it is believed, without wishing to necessarily be bound by any one particular theory, that the lipidation of the OspA may be providing the protective results.

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

1. Barbour, A. G. and Fish, D. The biological and social phenomenon of Lyme disease. *Science.* 1993, 260, 1610–1616
2. Fikrig, E., Barthold, S. W., Kantor, F. S. and Flavell, R. A. Protection of mice against the Lyme disease agent by immunizing with recombinant OspA. Science. 1990, 250, 553–556
3. Erdile, L. f., Brandt, M., Warakomski, D. J., Westrack, G. J., Sadziene, A., Barbour, A. G. and Mays, J. P. Role of attached lipid in immunogenicity of *Borrelia burgdorferi* OspA. *Infect. Immun.* 1993, 61, 81–90. See also U.S. Ser. No. 08/373,455.
4. Keller, D., Kister, F. T., Marks, D. H., Hosback, P., Erdile, L. F. and Mays, J. P. Safety and immunogenicity of a recombinant outer surface protein A Lyme vaccine. *J. Am. Med. Assoc.* 1994, 271, 1764
5. Fikrig, E., Barthold, S. w., Kantor, F. S., and Flavell, R. A. Protection of mice from Lyme *borreliosis* by oral vaccination with *Escherichia coli* expressing OspA. *J. Infect. Dis.* 1991, 164, 1224–1227
6. Dunne, M., Al-Ramadi, B. K., Barthold, S. W., Flavell, R. A. and Fikrig, e. Oral vaccination with an attenuated *Salmonella typhimurium* strain expressing *Borrellia burgdorferi* OspA prevents murine Lyme borreliosis. *Infect. Immun.* 1995, 63, 1611–1614
7. Langermann, S., Palaszynski, S., Sadziene, A., Stover, C. K. and Koenig, S. Systemic and mucosal immunity induced by BCG vector expressing outer-surface protein A of *Borrelia burgdorferi. Nature* (London). 1994, 372, 552–555
8. Wilske, B., Preac-Mursic, V.,Schierz, G., Kuhbek, R., Barbour, A. G. and Kramer. M. Antigenic variability of *Borrelia burgdorferi. Ann. N.Y. Acad. Sci.* 1988, 539, 126–143
9. Sadziene, A., Thomas, D. D. and Barbour, A. G. *Borrelia burgdorferi* mutant lacking Osp: biological and immunological characterization. *Infect. Immun.* 1995, 63, 1573–1580
10. Barbour, A. G. Immunochemical analysis of Lyme disease spirochaetes. *Yale J. Biol. Med.* 1984, 57, 581–586
11. Barbour, A. G., Tessier, S. L. and Stoenner, H. Variable major proteins of *Borrelia hermsii. J. Exp. Med.* 1982, 156, 1312–1324
12. Sadziene, A., Thompson, P. A. and Barbour, A. G. In vitro inhibition of *Borrelia burgdorferi* growth by antibodies. *J. Infect. Dis.* 1993, 167, 165–172
13. Dunn, J. J., Lade, B. N. and Barbour, A. G. Outer surface protein A (OspA) from the Lyme disease spirochete, *Borrelia burgdorferi*: high level expression and purification of a soluble recombinant form of OspA. *Protein Expression Purif.* 1990, 1, 159–168
14. Lee, C. K., Weltzin, R., Thomas, W. D., Kleanthous, H., Ermak, T. H., Soman, G., Hill, J. e., Ackerman, S. K. and Monath, T. P. Oral immunization with recombinant *Helicobacter pylori* urease induces secretory IgA antibodies and protects mice from challenge with *Helicobacter felis. J. Infect. Dis.* 1995, 172, 161–172
15. Sadziene, A., Rosa, P. A., Thompson, Hogan, D. M. and Barbour, A. G. Antibody-resistant mutants of *Borrelia burgdorferi*: in vitro selection and characterization. J. Exp. Med. 1992, 176, 799–809

The invention claimed is:

1. A method for inducing an immunological response, including OspA specific serum IgA antibodies in a mammalian host susceptible to Lyme disease or *Borrelia burgdorferi* infection comprising orally administering a composition comprising substantially pure outer surface protein A (OspA) and a carrier or diluent which is free of any immunogenicity-enhancing adjuvant.

2. The method of claim 1 wherein the OspA is lipidated OspA.

3. The method of claim 1 wherein the carrier or diluent is a liquid.

4. The method of claim 1 wherein the OspA is recombinant OspA.

5. The method of claim 4 wherein the OspA is lipidated.

6. The method of claim 5 wherein the OspA is obtained by: transforming a host organism by a plasmid containing a gene coding for a full-length wild-type *Borrelia burgdorferi* OspA lipoprotein and producing recombinant *Borrelia burgdorferi* OspA lipoprotein, and purifying the recombinant *Borrelia burgdorferi* OspA lipoprotein substantially free from other bacterial proteins, and from lipopolysaccharide, under non-denaturing conditions from a lysate of the host organism so as to obtain a purified recombinant *Borrella burgdorferi* OspA lipoprotein which remains lipidated and is in a form administrable to the host.

7. The method of claim 1 wherein the composition comprising substantially pure OspA and a carrier or diluent is a solution, suspension, emulsion, syrup, elixir, capsule, tablet, hard-candy-like preparation, or a solid food item.

* * * * *

UNITED STATES PATENT AND TRADEMARK OFFICE
CERTIFICATE OF CORRECTION

PATENT NO. : 7,094,391 B1  Page 1 of 1
APPLICATION NO. : 08/588637
DATED : August 22, 2006
INVENTOR(S) : Alan G. Barbour and Catherine J. Luke It is certified that error appears in the above-identified patent and that said Letters Patent is hereby corrected as shown below:

<u>In The Claims:</u>

Column 14, line 6, "*Borrella*" should read --*Borrelia*--

Signed and Sealed this

Twenty-sixth Day of December, 2006

JON W. DUDAS
*Director of the United States Patent and Trademark Office*